United States Patent [19]
Maurer et al.

[11] Patent Number: 5,981,438
[45] Date of Patent: Nov. 9, 1999

[54] 1-PHENYL-5-ANILINOTETRAZOLES

[75] Inventors: Fritz Maurer, Wuppertal, Germany; Kaori Kido; Yoshio Kurahashi, both of Oyama, Japan; Haruko Sawada, Yuki, Japan; Keiko Tanaka; Yuichi Otsu, both of Oyama, Japan; Yumi Hattori, Ibaraki, Japan; Katsuhiko Shibuya, Minamihkawachi-machi, Japan; Takahisa Abe, Oyama, Japan; Toshio Goto, Shimotsuga-gun, Japan; Seishi Ito, Oyama, Japan

[73] Assignee: Nihon Bayer Agrochem K.K., Tokyo, Japan

[21] Appl. No.: 09/009,860

[22] Filed: Jan. 22, 1998

[30] Foreign Application Priority Data

Jan. 28, 1997 [JP] Japan ........................... 9-27300

[51] Int. Cl.$^6$ ................. A01N 43/713; C07D 257/06
[52] U.S. Cl. ................... 504/253; 504/261; 514/381; 514/382; 514/340; 548/251; 548/252; 546/268.4
[58] Field of Search ...................... 514/381, 382, 514/340; 548/251, 252; 504/261, 253

[56] References Cited

U.S. PATENT DOCUMENTS

| | | | |
|---|---|---|---|
| 3,830,928 | 8/1974 | Mrozik | 424/269 |
| 4,036,849 | 7/1977 | Curran et al. | 260/308 D |

FOREIGN PATENT DOCUMENTS

| | | |
|---|---|---|
| 149269 | 7/1985 | European Pat. Off. . |
| 2203739 | 10/1988 | European Pat. Off. . |
| 1560988 | 2/1980 | United Kingdom . |

OTHER PUBLICATIONS

Ding et al., "Preparation of 1–Aryl–5–(N–aryl–N–benzoylamino)tetrazoles," Synthesis, vol. 9, pp. 823–824, Sep. 1977.

*Primary Examiner*—Johann Richter
*Assistant Examiner*—Jane C. Oswecki
*Attorney, Agent, or Firm*—Sprung Kramer Schaefer & Briscoe

[57] ABSTRACT

The present invention relates to novel 1-Phenyl-5-anilinotetrazoles of the formula (I):

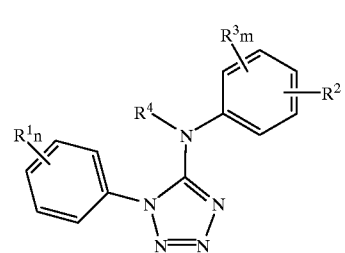

(I)

wherein, $R^1$, $R^2$, $R^3$, $R^4$, m and n have the meaning provided in the specification, precesses for their preparation and their use as microbiocides, insecticides and/or herbicides.

10 Claims, No Drawings

1-PHENYL-5-ANILINOTETRAZOLES

The present invention relates to novel 1-phenyl-5-anilinotetrazoles, to processes for their preparation and to their use as microbiocides, insecticides and/or herbicides.

Certain 1-phenyl-5-anilinotetrazoles are described in Collection of Czechoslovak Chemical Communications (1992), 57(5), 1065–71; Synthetic Communications (1990), 20(2), 217–26; Synthesis (1987), (9), 823–4; Monatschefte fuer Chemie (1983), 114(1), 65–70; Journal of Organic Chemistry (1980), 45(25), 5136–6; ibid. (1977), 42(23), 3709–13; Journal of Chemical Society, Perkin Transaction 1(1977), (11), 1241–3; Chem. Zvesti (1979), 33(4), 521–7; and the like. However, these prior art literature do not disclose their uses as agricultural chemicals.

There have now been found novel 1-phenyl-5-anilinotetrazoles of the formula (I)

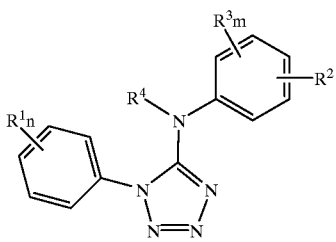

(I)

wherein $R^1$ is hydrogen, halogen, cyano, nitro, $C_{1-4}$ alkyl, $C_{1-4}$ haloalkyl, $C_{1-4}$ haloalkoxy or $C_{1-4}$ haloalkylthio, $R^2$ is cyano, nitro, $C_{1-4}$ haloalkyl, $C_{1-4}$ alkylsulfonyl, $C_{1-4}$ haloalkyl-sulfonyl, $C_{1-4}$ alkoxy-carbonyl, aminocarbonyl or aminothiocarbonyl, $R^3$ is halogen, $C_{1-4}$ haloalkyl or $C_{1-4}$ haloalkoxy, $R^4$ is hydrogen, cyano, $C_{1-4}$ alkyl, $C_{1-4}$ alkyl-carbonyl, $C_{1-4}$ alkoxy-carbonyl, $C_{1-4}$ alkylsulfonyl, $C_{1-4}$ alkoxy-$C_{1-4}$ alkyl-carbonyl, phenoxy-carbonyl which may be substituted by nitro or pyridylcarbonyl which may be substituted by halogen, n is 1, 2 or 3, and when n represents 2 or 3, two or three of $R^1$ may be same or different, and m is 1 or 2, and when m represents 2, two of $R^3$ may be same or different.

The novel 1-phenyl-5-anilinotetrazoles of the formula (I), according to the invention, can be obtained when a) in the case where $R^4$ is hydrogen:
compounds of the formula (II)

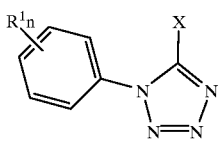

(II)

wherein $R^1$ and n are defined as above, and X is halogen or methylsulfonyl, are reacted with compounds of the formula (III)

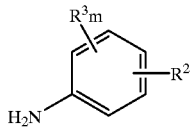

(III)

wherein $R^2$, $R^3$ and m are defined as above, the presence of a diluent, and, if appropriate, in the presence of an acid binding agent, or b) in the case where $R^4$ is $C_{1-4}$ alkyl or $C_{1-4}$ alkoxy-carbonyl:
compounds of the formula (IV)

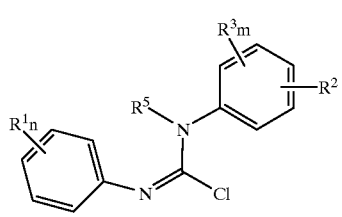

(IV)

wherein
$R^1$, $R^2$, $R^3$, m and n are defined as above, and
$R^5$ is $C_{1-4}$ alkyl or $C_{1-4}$ alkoxy-carbonyl, are reacted with sodium azide, in the presence of a diluent, or c) in the case where $R^4$ is hydrogen:
compounds of the formula (Ib)

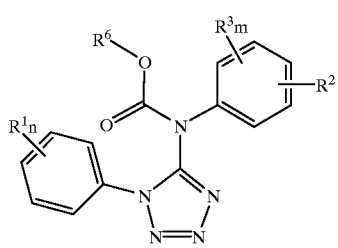

(Ib)

wherein $R^1$, $R^2$, $R^4$, and m are defined as above, and $R^6$ is $C_{1-4}$ alkyl or optionally nitro-substituted phenyl, are hydrolyzed, in the presence of a diluent, and, if appropriate, in the presence of a base, or d) in the case where $R^4$ is radicals as defined for the above $R^4$ with the exception of hydrogen and $C_{1-4}$ alkyl:
compounds of the formula (Ia)

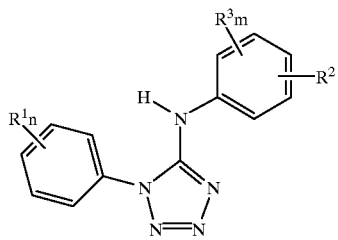

(Ia)

wherein $R^1$, $R^2$, $R^3$, n and m are defined as above, are reacted with compounds of the formula (V)

$$R^7-Y \quad (V)$$

wherein $R^7$ is radicals as defined for the above $R^4$ with the exception of hydrogen and $C_{1-4}$ alkyl, and Y is halogen, in the presence of a diluent, and, if appropriate, in the presence of an acid binding agent, or e) in the case where $R^4$ is $C_{1-4}$alkyl-carbonyl or $C_{1-4}$ alkoxy-$C_{1-4}$ alkyl-carbonyl: the above-mentioned compounds of the formula (Ia) are reacted with compounds of the formula (VI)

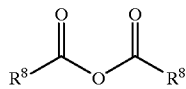

(VI)

wherein $R^1$ is $C_{1-4}$ alkyl or $C_{1-4}$ alkoxy-$C_{1-4}$ alkyl, optionally in the presence of a diluent and in the presence of an acid catalyst.

The 1-phenyl-5-anilinotetrazoles of the formula (I) according to the invention exhibit insecticidal action and/or fungicidal action and/or herbicidal action.

Surpassingly, the 1-phenyl-5-anilinotetrazoles of the formula (I) according to the invention have a very high insecticidal activity, fungicidal activity and/or herbicidal activity.

In this specification, the halogen in the terms "halogen", "haloalkyl" and "haloalkoxy" represents fluorine, chlorine, bromine or iodine, preferably being fluorine, chlorine or bromine.

The "alkyl" may be straight-chain or branched and includes, for example, methyl, ethyl, propyl, isopropyl, n-, iso-, sec- or tert-butyl, and the like.

The "alkoxy" may be straight-chain or branched and includes, for example, methoxy, ethoxy, propoxy, isopropoxy, n-, iso-, sec- or tert-butoxy, and the like.

The "haloalkyl" may be straight-chain or branched and includes, for example, trifluoromethyl, 2,2,2-trifluoroethyl, chloroethyl, and the like.

The "haloalkoxy" may be straight-chain or branched and includes, for example, trifluoromethoxy, 2,2,2-trifluoroethoxy, and the like.

The "haloalkylthio" may be straight-chain or branched and includes, for example, trifluoromethylthio, 2,2,2-trifluoroethylthio, and the like.

The "alkylsulfonyl" may be straight-chain or branched and includes, for example, methylsulfonyl, ethylsulfonyl, propylsulfonyl, isopropylsulfonyl, and the like.

The "haloalkylsulfonyl" may be straight-chain or branched and includes, for example, trifluoromethylsulfonyl, 2,2,2-trifluoroethylsulfonyl, and the like.

Among the 1-phenyl-5-anilinotetraozoles of the formula (I), the preferred compounds are those in which $R^1$ is hydrogen, halogen, cyano, nitro, $C_{1-3}$ alkyl, $C_{1-3}$ fluoroalkyl, $C_{1-3}$ fluoroalkoxy or $C_{1-3}$ fluoroalkylthio, $R^2$ is cyano, nitro, $C_{1-3}$ haloalkyl, $C_{1-3}$ alkylsulfonyl, $C_{1-3}$ haloalkylsulfonyl, $C_{1-3}$ alkoxy-carbonyl, aminocarbonyl or aminothiocarbonyl, $R^3$ is halogen, $C_{1-3}$ fluoroalkyl or $C_{1-3}$ fluoroalkoxy, $R^4$ is hydrogen, cyano, $C_{1-3}$ alkyl, $C_{1-3}$ alkyl-carbonyl, $C_{1-3}$ alkoxy-carbonyl, $C_{1-3}$ alkylsulfonyl, $C_{1-2}$ alkoxy-$C_{1-2}$ alkyl-carbonyl, optionally nitro-substituted phenoxycarbonyl or optionally chloro-substituted pyridylcarbonyl, n is 1 or 2, and when n represents 2, two of $R^1$ may be same or different, and m is 1 or 2, and when m represents 2, two of $R^3$ may be same or different.

Very particularly preferred 1-phenyl-5-anilinotetrazoles of the formula (I) are those wherein $R^1$ is hydrogen, fluorine, chlorine, bromine, cyano, nitro, methyl, trifluoromethyl, trifluoromethoxy or trifluoromethylthio, $R^2$ is cyano, nitro, trifluoromethyl, methylsulfonyl, ethylsulfonyl, trifluoromethylsulfonyl, methoxy-carbonyl, ethoxy-carbonyl, aminocarbonyl or aminothiocarbonyl, $R^3$ is fluorine, chlorine, bromine, trifluoromethyl or trifluoromethoxy, $R^4$ is hydrogen, cyano, methyl, methylcarbonyl, methoxycarbonyl, ethoxycarbonyl, methylsulfonyl, methoxymethylcarbonyl, phenoxycarbonyl, 4-nitrophenoxycarbonyl or 2,6-dichloro-4-pyridylcarbonyl, n is 1 or 2, and when n represents 2, two of $R^1$ may be same or different, and m is 1 or 2, and when m represents 2, two of $R^3$ may be same or different.

Specific examples of the 1-phenyl-5-anilinotetrazoles of the formula (I) according to the invention, which may be mentioned, are the compounds shown in the later-described Table 1.

In the above-mentioned process (a), if, for example, 5-chloro-1-phenyltetrazole and 4-amino-3-trifluoromethylbenzonitrile are used as starting materials, the course of the reaction can be represented by the following equation:

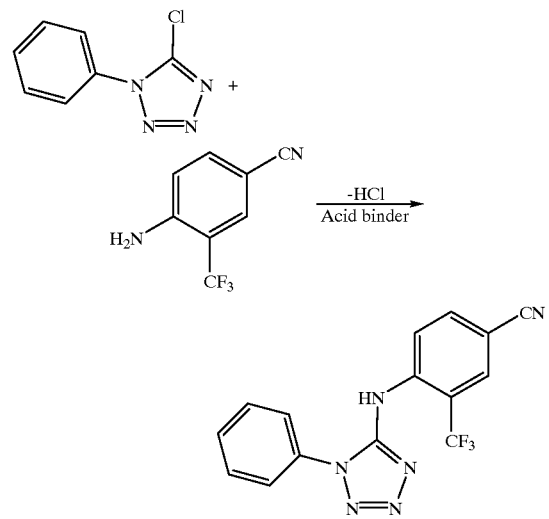

In the above-mentioned process (b), if, for example, N'-(4-fluorophenyl)-N-(4-cyano-2,5-difluorophenyl)-N-methyl-chloroformamidine and sodium azide are used as starting materials, the course of the reaction can be represented by the following equation:

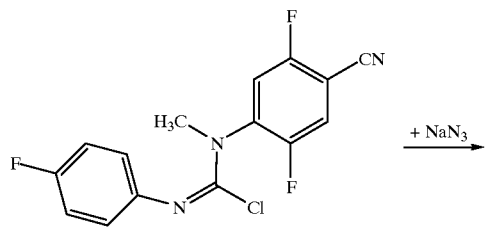

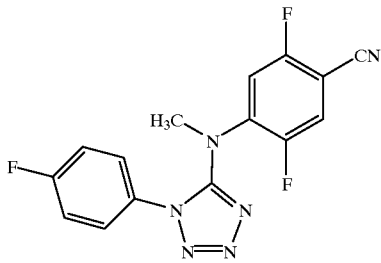

In the above-mentioned process (c), if, for example, 1-(4-trifluoromethylphenyl)-5-(2-chloro-4-trifluoromethyl-N-methoxycarbonyl-anilino)tetrazole is hydrolyzed, the course of the reaction can be represented by the following equation:

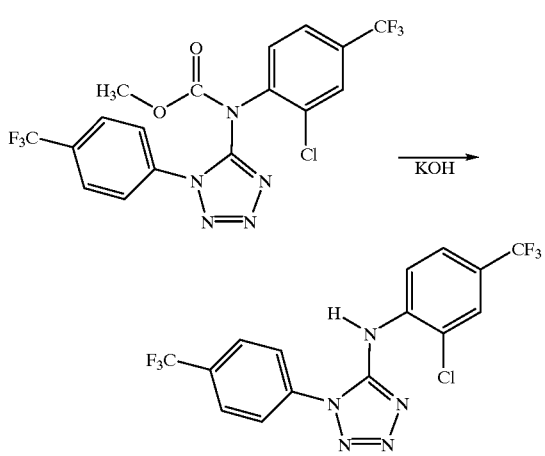

In the above-mentioned process (d), if, for example, 1-(4-trifluoromethylphenyl)-5-(4-cyano-2,5-difluoroanilino)tetrazole and methanesulfonyl chloride are used as starting materials, the course of the reaction can be represented by the following equation:

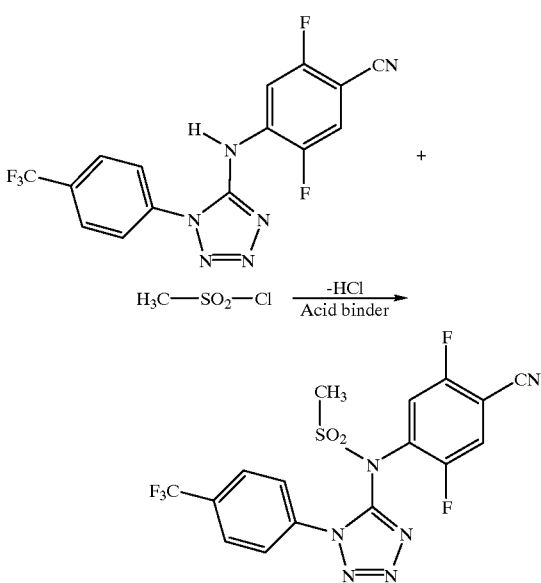

In the above-mentioned process (e), if, for example, 1-(4-trifluoromethoxyphenyl)-5-(4-cyano-2,5-difluoroanilino)tetrazole and acetic anhydride are used as starting materials, the course of the reaction can be represented by the following equation:

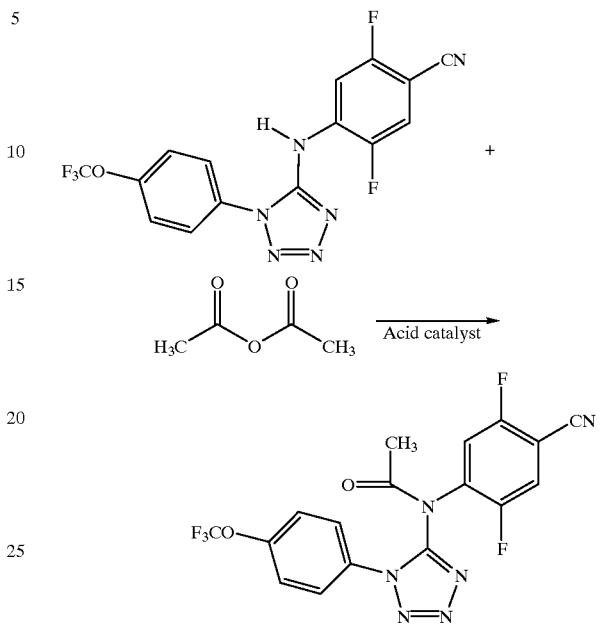

In the process (a), the starting materials of the formula (II) mean compounds based on the above definition of $R^1$, n and X, preferably substituents based on the above preferred definitions of $R^1$ and n, and X preferably represents chlorine or bromine.

The compounds of the formula (II) used as the starting material include:
5-chloro-1-phenyltetrazole,
5-chloro-1-(4-fluorophenyl)tetrazole,
5-chloro-1-(4-chlorophenyl)tetrazole,
5-chloro-1-(4-bromophenyl)tetrazole,
5-chloro-1-(4-trifluoromethylphenyl)tetrazole,
5-chloro-1-(4-trifluoromethoxylphenyl)tetrazole,
5-chloro-1-(3-chloro-4-trifluoromethylphenyl)tetrazole,
5-methylsulfonyl-1-(3-fluorophenyl)tetrazole,
and the like.

The compounds of the formula (II) are described, as well as processes for their preparation, in Japanese Patent Kokai Publication Sho 56-86175, DE-A-1251327 and GB-A-1128025, or can be synthesized in the manner similar to those described in these references.

In the process (a) according to the invention, the starting materials of the formula (III) mean compounds based on the above definitions of $R^2$, $R^3$ and m, preferably substituents based on the above preferred definitions of $R^2$, $R^3$ and m.

The compounds of the formula (III) used as the starting material are well known in the field of organic chemistry and examples thereof include, for instance,
4-amino-3-trifluoromethyl-benzonitrile,
4-amino-2,5-difluoro-benzonitrile,
2-chloro-4-trifluoromethyl-aniline,
2-chloro-4-trifluoromethylsulfonylaniline,
2-chloro-4-methylsulfonylaniline, and the like.

In the process (b) according to the invention, the starting materials of the formula (IV) mean compounds based on the $R^1$, $R^2$, $R^3$, m, n and $R^5$, preferably substituents based on the above preferred definitions of $R^1$, $R^2$, $R^3$ m and n, and $R^5$ preferably represents $C_{1-3}$ alkyl or $C_{1-3}$ alkoxy-carbonyl.

In the process (b), examples of the compounds of the formula (IV) used as the starting material include:

N'-(4-fluorophenyl)-N-(4-cyano-2,5-difluorophenyl)-N-methylchloroformamidine,

N'-(4-trifluoromethylphenyl)-N-(4-cyano-2,5-difluorophenyl)-N-methylchloroformamidine, N'-(4-trifluoromethylphenyl)-N-(2-chloro-4-trifluoromethylphenyl)-N-methylchloroformamidine, and the like.

The compounds of the formula (IV) can be produced, for instance, by the processes described in Journal of Organic Chemistry, (1977), 42(23), 3709–3713 and the like, and can be synthesized, for example, by the following method.

Compounds of the formula (VII)

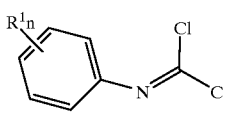

(VII)

wherein $R^1$ and n are as defined above, are reacted with compounds of the formula (VIII)

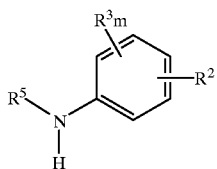

(VIII)

wherein $R^2$, $R^3$, m and $R^5$ are as defined above. in the presence of a diluent, and, if appropriate, in the presence of an acid binding agent.

The compounds of the formula (VII) and (VIII) are well known compounds in the field of organic chemistry.

In the process (c) according to the invention, the starting materials of the formula (Ib) mean compounds based on the above definitions of $R^1$, $R^2$, $R^3$, $R^6$, m and n, preferably substituents based on the above preferred definitions of $R^1$, $R^2$, $R^3$ m and n, and $R^6$ preferably represents $C_{1-3}$ alkyl, phenyl or 4-nitrophenyl.

The compounds of the formula (Ib) used as the starting material are the compounds according to the invention, which can be synthesized by the above process (b).

Specific examples thereof include:

1-(4-fluorophenyl)-5-(2-chloro-4-trifluoromethyl-N-methoxycarbonylanilino) tetrazole, 1-(4-trifluoromethylphenyl)-5-(2-chloro-4-trifluoromethyl-N-methoxycarbonylanilino)tetrazole, 1-(4-trifluoromethoxyphenyl)-5-(2-chloro-4-trifluoromethyl-N-methoxycarbonylanilino)tetrazole and the like.

In the processes (d) and (e) according to the invention, starting materials of the formula (Ia) mean compounds based on the above definitions of $R^1$, $R^2$, $R^3$, m and n, preferably substituents based on the above preferred definitions.

The compounds of the formula (Ia) used as the starting material are compounds according to the invention, which can be synthesized by the above processes (a) or (c).

Specific examples of the compounds of the formula (Ia) include:

1-(4-trifluoromethylphenyl)-5-(4-cyano-2,5-difluoromethylanilino)tetrazole, 1-(4-trifluoromethoxyphenyl)-5-(4-cyano-2,5-difluoromethylanilino)tetrazole, and the like.

In the process (d) according to the invention, the starting materials of the formula (V) mean compounds based on the above definitions of $R^7$ and Y, $R^7$ preferably represents cyano, $C_{1-3}$ alkyl-carbonyl, $C_{1-3}$ alkoxy-carbonyl, $C_{1-3}$ alkylsulfonyl, phenoxycarbonyl which may be substituted by nitro, or pyridylcarbonyl which may be substituted by chlorine. Y preferaily represents chlorine or bromine.

The compounds of the formula (V) used as the starting materials are well known in the field of organic chemistry, and examples thereof include acetyl chloride, propionyl chloride, methoxyacetyl chloride, methyl chloroformate, ethyl chloroformate, cyanogen bromide, methanesulfonyl chloride, and the like.

In the process (e) according to the invention, the starting materials of the formula (VI) mean compounds based on the above definitions of $R^8$, preferably represents $C_{1-3}$ alkyl or $C_{1-2}$ alkoxy-$C_{1-2}$ alkyl The compounds of the formula (VI) used as the starting material are well known in the field of organic chemistry and examples thereof include acetic anhydride.

The reaction of the above process (a) can be carried out in an appropriate diluent. Examples of suitable diluents are aliphatic, alicyclic or aromatic hydrocarbons (which may optionally be chlorinated) such as pentane, hexane, cyclohexane, petroleum ether, ligroin, benzene, toluene, xylene, dichloromethane, chloroform, carbon tetrachloride, 1,2-dichloroethane, chlorobenzene and dichlorobenzene; ethers such as diethyl ether, methyl ethyl ether, diisopropyl ether, dibutyl ether, dioxane, dimethoxyethane (DME), tetrahydrofuran (THF) and diethylene glycol dimethyl ether (DGM); ketones such as acetone, methyl ethyl ketone (MEK), methyl-isopropyl ketone and methyl isobutyl ketone (MIBK); nitriles such as acetonitrile, propionitrile and acrylonitrile; esters such as ethyl acetate and amyl acetate; acid amides such as dimethylformamide (DMF), dimethylacetamide (DMA), N-methylpyrrolidone, 1,3-dimethyl-2-imidazolidinone and hexamethylphosphoric triamide (PA); sulfones and sulfoxides such as dimethyl sulfoxide (DMSO) and sulfolan; etc.

The reaction of the process (a) can be carried out in the presence of an acid binding agent. Examples of suitable acid binding agents are inorganic bases, for example, hydroxides, carbonates and bicarbonates of alkali metals or alkaline earth metals and alkoxides, such as sodium hydrogencarbonate, potassium hydrogencarbonate, sodium carbonate, lithium hydroxide, sodium hydroxide, potassium hydroxide, calcium hydroxide, sodium tert-butoxide and potassium tert-butoxide; inorganic alkali metal amides, such as lithium amide, sodium amide and potassium amide; organic bases, for example, alcoholates, tertiary amines, dialkylaminoanilines and pyridines, such as triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo [2,2,2] octane (DABCO) and 1,8-diazabicyclo[5,4,0]undec-7-ene (DBU); organic lithium compounds, such as methyl lithium, n-butyl lithium, sec-butyl lithium, tert-butyl lithium, phenyllithium, dimethyl copper lithium, lithium diisopropylamide lithium cyclohexylisopropylamide, lithium dicyclohexylamide, n-butyl lithium-DABCO, n-butyl lithium-DBU and n-butyl lithium-TMEDA.

The reaction of the process (a) can be conducted at a temperature within a substantially broad range, but it is generally possible to employ a reaction temperature of about −20 to about 100° C., preferably about −5 to about 80° C.

Further, the reaction should preferably be conducted under normal pressure but it may optionally be operated under elevated or reduced pressure.

For carrying out the process (a), for instance, 1 mole of the compound of the formula (II) can be reacted with 1 to 1.1 molar amounts of the compound of the formula (III) in a diligent such as tetrahydrofuran, in the presence of an acid binding agent to thereby obtain the desired compound.

The reaction of the above process (b) can be carried out in an appropriate diluent. Examples of suitable diluents are water; aliphatic, alicyclic or aromatic hydrocarbons (which may optionally be chlorinated) such as pentane, hexane, cyclohexane, petroleum ether, ligroin, benzene, toluene, xylene, dichloromethane, chloroform, carbon tetrachloride, 1,2-dichloroethane, chlorobenzene and dichlorobenzene; ethers such as ethyl ether, methyl ethyl ether, isopropyl ether, butyl ether, dioxane, dimethoxyethane (DME), tetrahydrofuran (THF) and diethylene glycol dimethyl ether (DGM); ketones such as acetone, methyl ethyl ketone (MEK), methyl-isopropyl ketone and methyl isobutyl ketone (MIBK); nitriles such as acetonitrile, propionitrile and acrylonitrile; alcohols such as methanol, ethanol, isopropanol, butanol and ethylene glycol; esters such as ethyl acetate and amyl acetate; acid amides such as dimethylformamide (DMF), dimethylacetamide (DMA), N-methylpyrrolidone, 1,3-dimethyl-2-imidazolidinone and hexamethylphosphoric triamide (HMPA); sulfones and sulfoxides such as dimethyl sulfoxide (DMSO) and sulfolan; etc.

The reaction of the process (b) can be conducted at a temperature within a substantially broad range, but it is generally possible to employ a reaction temperature of about 0 to about 120° C., preferably about 20 to about 100° C. Further, the reaction should preferably be conducted under normal pressure but it may optionally be operated under elevated or reduced pressure.

For carrying out the process (b), for instance, 1 mole of the compound of the formula (IV) can be reacted with 1 to 1.5 molar amounts of sodium azide in a diligent such as a mixed solvent of acetone and water to thereby obtain the desired compound.

The reaction of the above process (c) can be carried out in an appropriate diluent. Preferred examples of suitable diluents are water or alcohols such as methanol, ethanol, isopropanol, butanol and ethylene glycol. However, other diluents can also be used and examples thereof are aliphatic, alicyclic or aromatic hydrocarbons (which may optionally be chlorinated) such as pentane, hexane, cyclohexane, petroleum ether, ligroin, benzene, toluene, xylene, dichloromethane, chloroform, carbon tetrachloride, 1,2-dichloroethane, chlorobenzene and dichlorobenzene; ethers such as diethyl ether, methyl ethyl ether, diisopropyl ether, dibutyl ether, dioxane, dimethoxyethane (DME), tetrahydrofuran (THF) and diethylene glycol dimethyl ether (DGM); ketones such as acetone, methyl ethyl ketone (MEK), methyl-isopropyl ketone and methyl isobutyl ketone (MIBK); nitriles such as acetonitrile, propionitrile and acrylonitrile; esters such as ethyl acetate and amyl acetate; acid amides such as dimethylformamide (DMF), dimethylacetamide (DMA), N-methylpyrrolidone, 1,3-dimethyl-2-imidazolidinone and hexamethylphosphoric triamide (HMPA); sulfones and sulfoxides such as dimethyl sulfoxide (DMSO) and sulfolan; etc.

The reaction of the process (c) can preferably be carried out in the presence of an inorganic base. Examples of suitable inorganic bases are hydroxides, carbonates and bicarbonates of alkali metals and alkaline earth metals, such as sodium hydrogencarbonate, potassium hydrogencarbonate, sodium carbonate, potassium carbonate, lithium hydroxide, sodium hydroxide, potassium hydroxide and calcium hydroxide.

The reaction of the process (c) can be conducted at a temperature within a substantially broad range, but it is generally possible to employ a reaction temperature of about 0 to about 150° C., preferably about 20 to about 100° C. Further, the reaction should preferably be conducted under normal pressure but it may optionally be operated under elevated or reduced pressure.

For carrying out the process (c), for instance, 1 mole of the compound of the formula (Ib) can be reacted with 1 to 3 molar amounts of a base in a diligent such as methanol to thereby obtain the desired compound.

The reaction of the above process (d) can be carried out in an appropriate diluent. Examples of suitable diluents are aliphatic, alicyclic or aromatic hydrocarbons (which may optionally be chlorinated) such as pentane, hexane, cyclohexane, petroleum ether, ligroin, benzene, toluene, xylene, dichloromethane, chloroform, carbon tetrachloride, 1,2-dichloroethane, chlorobenzene and dichlorobenzene; ethers such as diethyl ether, methyl ethyl ether, diisopropyl ether, dibutyl ether, dioxane, dimethoxyethane (DME), tetrahydrofuran (THF) and diethylene glycol dimethyl ether (DGM); ketones such as acetone, methyl ethyl ketone (MEK), methyl-isopropyl ketone and methyl isobutyl ketone (MIBK); nitrites such as acetonitrile, propionitrile and acrylonitrile; esters such as ethyl acetate and amyl acetate; acid amides such as dimethylformamide (DMF), dimethylacetamide (DMA), N-methylpyrrolidone, 1,3-dimethyl-2-imidazolidinone and hexamethylphosphoric triamide (HMPA); sulfones and sulfoxides such as dimethyl sulfoxide (DMSO) and sulfolan; etc.

The reaction of the process (d) can be carried out in the presence of an acid binding agent. Examples of suitable acid binding agents are inorganic bases, for example, hydroxides, carbonates and bicarbonates of alkali metals or alkaline earth metals, such as sodium hydrogencarbonate, potassium hydrogencarbonate, sodium carbonate, potassium carbonate, lithium hydroxide, sodium hydroxide, potassium hydroxide and calcium hydroxide; inorganic alkali metal amides, such as lithium amide, sodium amide and potassium amide; metal hydrides, such as lithium hydride, sodium hydride, potassium hydride and calcium hydride; organic bases, for example, alkoxides, tertiary amines, dialkylaminoanilines and pyridines, such as sodium tert-butoxide, potassium tert-butoxide, triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO) and 1,8-diazabicyclo[5,4,0]undec-7-ene (DBU); organic lithium compounds, such as methyl lithium, n-butyl lithium, sec-butyl lithium, tert-butyl lithium, phenyllithium, dimethyl copper lithium, lithium diisopropylamide, lithium cyclohexylisopropylamide, lithium dicyclohexylamide, n-butyl lithium-DABCO, n-butyl lithium-DBU and n-butyl lithium-TMEDA.

The reaction of the process (d) can be conducted at a temperature within a substantially broad range, but it is generally possible to employ a reaction temperature of about 0 to about 120° C., preferably about 10 to about 100° C. Further, the reaction should preferably be conducted under normal pressure but it may optionally be operated under elevated or reduced pressure.

For carrying out the process (d), for instance, 1 mole of the compound of the formula (Ia) can be reacted with 1 to 1.5 molar amounts of the compound of the formula (V) in a diligent such as tetrahydrofuran, in the presence of an acid binding agent to thereby obtain the objective compound.

The reaction of the above process (e) can be carried out without a diluent or in an appropriate diligent. Examples of suitable diluents are aliphatic, alicyclic or aromatic hydrocarbons (which may optionally be chlorinated) such as pentane, hexane, cyclohexane, petroleum ether, ligroin, benzene, toluene, xylene, dichloromethane, chloroform, carbon tetrachloride, 1,2-dichloroethane, chlorobenzene and dichlorobenzene; ethers such as ethyl ether, methyl ethyl ether, isopropyl ether, butyl ether, dioxane, dimethoxyethane (DME), tetrahydrofuran (THF) and diethylene glycol dimethyl ether (DGM); ketones such as acetone, methyl ethyl ketone (MEK), methylisopropyl ketone and methyl isobutyl ketone (MIBK); nitriles such as acetonitrile, propionitrile and acrylonitrile; alcohols such as methanol, ethanol, isopropanol, butanol and ethylene glycol; esters such as ethyl acetate and amyl acetate; acid amides such as dimethylformamide (DMF), dimethylacetamide (DMA), N-methylpyrrolidone, 1,3-dimethyl-2-imidazolidinone and hexamethylphosphoric triamide (HMPA); sulfones and sulfoxides such as dimethyl sulfoxide (DMSO) and sulfolan; etc.

The reaction of the process (e) can be carried out in the presence of an acid catalyst. Examples of suitable acid catalysts are mineral acids such as hydrochloric acid, sulfuric acid, nitric acid, hydrobromic acid, sodium hydrogensulfite; organic acids such as formic acid, acetic acid, trifluoroacetic acid, propionic acid, methanesulfonic acid, benzenesulfonic acid, p-toluenesulfonic acid; organic amine hydrochloric acid salts such as a pyridine-hydrochloric acid salt, triethylamine-hydrochloric acid salt; etc.

The reaction of the process (e) can be conducted at a temperature within a substantially broad range, but it is generally possible to employ a reaction temperature of about 0 to about 150° C., preferably about 20 to about 120° C. Further, the reaction should preferably be conducted under normal pressure but it may optionally be operated under elevated or reduced pressure.

For carrying out the process (e), for instance, an excessive amount of the compound of the formula (VI), which also may act as a solvent, can be reacted with the compound of the formula (Ia) in the presence of an acid catalyst to thereby obtain the desired compound.

The 1-phenyl-5-anilinotetrazoles of the formula (I) according to the invention exhibit powerful microbiocidal action, insecticidal action and/or herbicidal action. Further, the 1-phenyl-5-anilinotetrazoles of the formula (I) according to the invention do not exhibit phytotoxicity against cultivated plants. Thus, they can be used as microbiocides, insecticides and/or herbicides.

The 1-phenyl-5-anilinotetrazoles of the formula (I) according to the invention exhibit a powerful microbicidal action and can be employed in practice for combating undesired microorganisms. The 1-phenyl-5-anilinotetrazoles of the formula (I) are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonoadaceae, Rhizobiaceae, Enterobacteriaceae, Corynebacteriaceae and Streptomycetaceae.

Some causative organisms of fungal and bacterial diseases included under the abovementioned main headings, are mentioned below as non-limiting examples: Xanthomonas species, such as, for example, *Xanthomonas campestris* pv. oryzae; Pseudomonas species, such as, for example, *Pseudomonas syringae* pv. lachrymans; Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora cubensis;* Plasmopara species, such as, for example, *Plasmopara viticola;* Peronospora species, such as, for example, *Peronospora pisior* pv. brassicae; Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teresor* pv. graminea; (Conidial form: Drechslera, Synonym: Helminthosporium); Cochliobolus species, such as, for example, *Cochliobolus sativus;* Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nudaor, Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae;* Pseudocercosporella species, such as, for example, *Pseudocercosporella herpotrichoides.*

The good toleration, by plants, of the 1-phenyl-5-anilinotetrazoles of the formula (I), at the concentrations required for combating plant diseases, permits treatment of above-ground parts of plants, of vegetative propagation stock and seeds, and of the soil.

The 1-phenyl-5-anilinotetrazoles of the formula (I) have a favorable level of toxicity to warm-blooded animals, and can be used for combating arthropod pests, especially insects which are encountered in agriculture, in forestry, in the protection of stored products and of materials, and in the hygiene field. They are active against normally sensitive and resistant species and against all or some stages of development.

The above-mentioned pests include:

from the class of the Isopoda, for example, *Oniscus Asellus, Armadillidium vulgareand* and *Porcellio scaber;* from the class of the Diplopoda, for example, *Blaniulus guttulatus;* from the class of the Chilopoda, for example, *Geophilus carpophagus* and Scutigera spec.;

from the class of the Symphyla, for example, *Scutigerella immaculata;* from the order of the Thysanura, for example, *Lepisma saccharina* from the order of the Collembola, for example, *Onychiurus armatus;* from the order of the Orthoptera; for example, *Blatta orientalis, Periplaneta americana Leucophaea maderae, Blattella germanica, Acheta domesticus,* Gryllotalpa spp., *Locusta migratoria, migratorioides, Melanoplus differentialis* and *Schistocerca gregaria;* from the order of the Dermaptera, for example, *Forficula auricularia;* from the order of the Isoptera, for example, Reticulitermes spp.;

from the order of the Anoplura, for example, *Phylloxera vastatrix,* Pemphigus spp., *Pediculus humanus corporis,* Haematopinus spp. and Linognathus spp.;

from the order of the Mallophaga, for example, Trichodectes spp. and Damalinea spp.;

from the order of the Thysanoptera, for example, *Hercinothrips femoralis* and *Thrips tabaci,* from the order of the Heteroptera, for example, Eurygaster spp., *Dysdercus intermedius, Piesmia guadrata, Cimex lectularius, Rhodnius prolixus* and Triatoma spp.;

from the order of the Homoptera, for example, *Aleurodes brassicae, Bemisia tabaci Trialeurodes vaporariorum, Aphis gossypii, Brevicoryne brassicae, Cryptomyzus ribis, Aphis fabae Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cinciceps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenopterafor example, Diprion spp., Hoplocampa spp, Lasius spp., *Monomorium pharaonis* and Vespa spp.;

from the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

Some of the 1-phenyl-5-anilinotetrazoles of the formula (I) according to the invention can be used as defoliants, desiccants, agents for destroying broad-leaved plants and, especially, as weedkillers.

By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the 1-phenyl-5-anilinotetrazoles of the formula (I) according to the invention is in no way restricted to these genera, but also extends in the same manner to other plants.

The 1-phenyl-5-anilinotetrazoles of the formula (I) are suitable, depending on the concentration, for the total combating of weeds, for example on industrial terrain and rail tracks, and on paths and squares with or without tree plantings. Equally, the 1-phenyl-5-anilinotetrazoles of the formula (I) can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The 1-phenyl-5-anilinotetrazoles of the formula (I) can be converted into the customary formulations, such as solutions, emulsions, wettable powders, suspensions, powders, foams, pastes, granules, tablets, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the 1-phenyl-5-anilinotetrazoles of the formula (I) with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl-isobutyl ketone or cyclohexanone, or strongly polar solvents, such as dimethylformamide and dimethylsulfoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products.

Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dye stuffs, azo dye stuffs or metal phthalocyanine dye stuffs, and trace nutrients, such as salts of iron, manganese boron, copper, cobalt, molybdenum and zinc.

The formulations in general contain from 0.1 to 95 percent by weight of active compound, preferably from 0.5 to 90 percent by weight.

The 1-phenyl-5-anilinotetrazoles of the formula (I) according to the invention can be present in their commercially available formulations and in the use forms prepared with these formulations, as a mixture with other active compounds, such as insecticides, attractants, sterilants, miticides, nematocides, fungicides, growth-regulating substances or herbicides. The mixable insecticides include, for example, organic phosphate, carbamates, carboxylates, chlorinated hydrocarbons and insecticidal substances produced by microorganisms.

When the 1-phenyl-5-anilinotetrazoles of the formula (I) are mixed with herbicides, the following known herbicides can be exemplified.

for controlling weeds in cereals cultivation,
4-amino-6-(1,1-dimethylethyl)-3-ethylthio-1,2,4-triazin-5 (4H)-one, 1-amino-6-ethylthio-3-(2,2-dimethylpropyl)-1,3,5-triazin-2,4(1H,3H)-dione,
N-(2-benzothiazolyl)-N,N'-dimethyl urea, etc.
for controlling weeds in cultivation of *Saccharum officinarum*:
4-amino-3-methyl-6-phenyl-1,2,4-triazin-5(4H)-one, etc.
for controlling weeds in cultivation of Glycine:
4-amino-6-(1,1-dimethylethyl)-3-methylthio-1,2,4-triazin-5 (4H)-one, etc.

The 1-phenyl-5-anilinotetrazoles of the formula (I) according to the invention can further be present as a mixture with synergistic agents. Synergistic agents are compounds which increase the action of the active compounds, without it being necessary for the synergistic agent added to be active itself.

The content of the 1-phenyl-5-anilinotetrazoles of the formula (I) according to the invention in their commercially available use form can be varied within wide limits, for instance within the range of from 0.0000001 to 100% by weight, preferably between 0.00001 and 1% by weight.

The 1-phenyl-5-anilinotetrazoles of the formula (I) according to the invention can be employed against pests, in a customary manner appropriate for the use forms. For combating hygiene pests and pests of stored cereals, the 1-phenyl-5-anilinotetrazoles of the formula (I) according to the invention are extremely excellent in stability to alkali on limed substances and in residual action on wood and soil.

When the 1-phenyl-5-anilinotetrazoles of the formula (I) according to the invention are used as herbicides, they can be applied at any stage of pre-emergence or post-emergence of plants. Also, they can be incorporated into the soil before sowing.

The application amount of the 1-phenyl-5-anilinotetrazoles of the formula (I) may be varied within a substantial range, and it basically varies depending on the desired properties of effect. But when the 1-phenyl-5-anilinotetrazoles of the formula (I) are used as herbicides, the application amount as the 1-phenyl-5-anilinotetrazoles of the formula (I) can be exemplified, for example, by about 0.001 kg/ha to about 5 kg/ha, preferably about 0.1 kg/ha to about 2 kg/ha.

Then, the following Examples illustrate the invention, but they should not be regarded as limiting the scope of the invention.

SYNTHESIS EXAMPLE 1

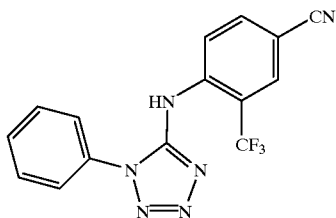

4-Amino-3-trifluoromethyl-benzonitrile (0.9 g) was added to a tetrahydrofuran solution (25 ml) of sodium hydride (0.5 g; 60% in oil) at room temperature. The mixture was stirred at room temperature for about 10 minutes until the generation of hydrogen gas was ceased. Then, 5-chloro-1-phenyltetrazole (0.9 g) was added thereto and the mixture was stirred for 2 hours. The reaction solution was poured into 100 ml of ice water and the organic layer was distilled off under reduced pressure. Activated carbon was added to the aqueous layer and the aqueous layer was filtered. Then, the pH of the filtrate was adjusted to 2–3 with concentrated hydrochloric acid. The precipitated crystals were collated by filtration and washed with water and n-hexane to obtain 1-phenyl-5-(4-cyano-2-trifluoromethylanilino)tetrazole (1.5 g).

melting point: 154–156° C.

SYNTHESIS EXAMPLE 2

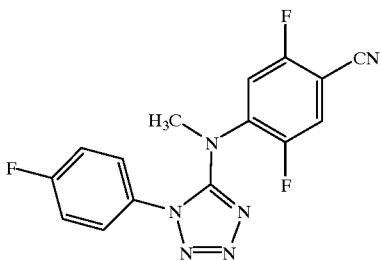

4-Methylamino-2,5-difluorobenzonitrile was added to a tetrahydrofuran solution (25 ml) of sodium hydride (0.4 g; 60% in oil). Until the generation of hydrogen gas was ceased, stirring was continued while keeping at 0 to 5° C. for about 10 minutes. Then, 4-fluorophenyl-isocyanide dichloride was added thereto and stirring was continued at room temperature for 3 hours. After activated carbon was added to the reaction solution, the solution was filtered and the filtrate was distilled off under reduced pressure. Then, the resulting residue was dissolved in acetone (30 ml). An aqueous solution (6 ml) of sodium azide (0.6 g) was added thereto and the mixture was heated under refluxing for 3 hours. After the completion of the reaction, water (80 ml) was added thereto and then the organic solvent was distilled off under reduced pressure. The precipitated crystals was collected by filtration and washed with water and n-hexane to obtain 1-(4-fluorophenyl)-5-(4-cyano-2,5-difluoro-N-methyl-anilino) tetrazole (2.3 g).

melting point: 162.5° C.

SYNTHESIS EXAMPLE 3

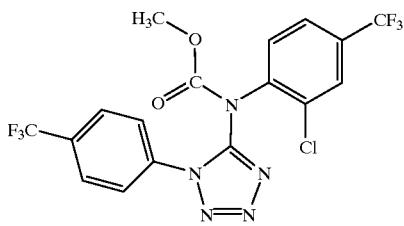

Methyl-N-(2-chloro-4-trifluoromethylphenyl)carbamate (2.0 g) was added to a tetrahydrofuran solution (25 ml) of sodium hydride (0.4 g; 60% in oil) at 0 to 5° C. Until the generation of hydrogen was ceased, stirring was continued while keeping at 0 to 5° C. for about 10 minutes. Then, 4-trifluoromethylphenyl-isocyanide dichloride (1.9 g) was added thereto and stirring was continued at room temperature for 3 hours. Activated carbon was added to the reaction solution, the solution was filtered and then the filtrate was distilled off under reduced pressure. The resulting residue was dissolved in acetone (30 ml). A water (7 ml) solution of sodium azide (0.65 g) was added thereto and the mixture was heated under refluxing for 3 hours. After the completion of the reaction, water (80 ml) was added thereto and extracted with dichloromethane. After drying over anhydrous sodium sulfate, dichloromethane was distilled off under reduced pressure. The resulting residue was dissolved in ethanol (15 ml) and then hexane (30 ml) was added thereto. The precipitated crystals were collected by filtration and washed with a mixed solution of ethanol: hexane (1:2) to obtain 1-(4-trifluoromethylphenyl)-5-(2-chloro-4-trifluoromethyl-N-methoxycarbonylanilino)tetrazole (1.8 g).

melting point: 111–112° C.

SYNTHESIS EXAMPLE 4

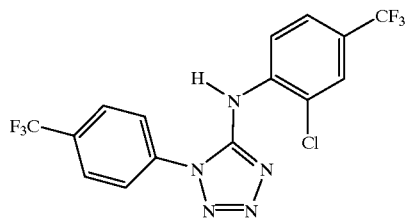

A mixed solution of 1-(4-trifluoromethylphenyl)-5-(2-chloro-4-trifluoromethyl-N-methoxycarbonyl-anilino) tetrazole (1.2 g), methanol (15 ml) and potassium hydroxide (0.4 g) was stirred at room temperature for 3 hours. After the completion of the reaction, hydrochloric acid (5%; 80 ml) was added thereto. The precipitated crystals were collected by filtration and washed with water to obtain 1-(4-trifluoromethylphenyl)-5-(2-chloro-4-trifluoromethylanilino)tetrazole (1.0 g).

melting point: 115.5–116.5° C.

SYNTHESIS EXAMPLE 5

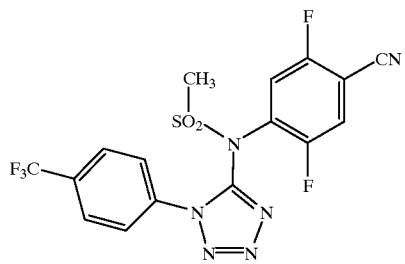

1-(4-Trifluoromethylphenyl)-5-(4-cyano-2,5-difluorophenylamino)tetrazole (1.5 g) was added to a tetrahydrofuran solution (25 ml) of sodium hydride (0.2 g; 60% in oil) at room temperature. Stirring was continued at room temperature for about 5 minutes until the generation of hydrogen gas was ceased. Then, methanesulfonyl chloride (0.5 g) was added thereto and stirring was continued at room temperature for about 24 hours. After the completion of the reaction, the solvent was distilled off under reduced pressure. Water was added to the resulting residue which as extracted twice with ethyl acetate. After the organic layer was dried over anhydrous sodium sulfate, the solvent was distilled off under reduced pressure. The resulting residue was dissolved in hot ethanol. After cooling, the precipitated crystals were collected by filtration and washed successively with cold ethanol and n-hexane to obtain 1-(4-trifluoromethylphenyl)-5-(4-cyano-2,5-difluoro-N-methylsulfonyl-anilino)tetrazole (1 g).

melting point: 129.5–130.5° C.

SYNTHESIS EXAMPLE 6

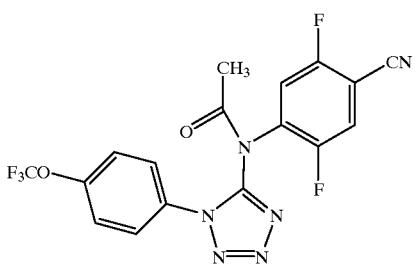

A mixed solution of acetic anhydride (15 ml), 1-(4-trifluoromethoxyphenyl)-5-(4-cyano-2,5-difluoroanilino)tetrazole (1.5 g) and concentrated sulfuric acid (1 ml) was stirred at 70 to 80° C. for 1 hour. After unreacted acetic anhydride was distilled off under reduced pressure, the residue was washed with water and n-hexane to obtain 1-(4-trifluoromethoxyphenyl)-5-(4-cyano-2,5-difluoro-N-acetylanilino)tetrazole (1.55 g).

melting point: 108–110.5° C.

The following Table 1 shows the compounds obtained in the same manner as described in the Synthesis Examples 1 to 6, together with the compounds obtained in the above Synthesis Examples 1 to 6.

TABLE 1

| Compound No. | $R^1n$ | $R^2$ | $R^3m$ | $R^4$ | melting point (° C.) or refractive index ($n^{20}_D$) |
|---|---|---|---|---|---|
| 1 | H | 4-CN | 2-$CF_3$ | H | 154–156 |
| 2 | 4-F | 4-CN | 2,5-$F_2$ | $CH_3$ | 162.5 |
| 3 | 4-$CF_3$ | 4-$CF_3$ | 2-Cl | $COOCH_3$ | 111–112 |
| 4 | 4-$CF_3$ | 4-$CF_3$ | 2-Cl | H | 115.5–116.5 |
| 5 | 4-$CF_3$ | 4-CN | 2,5-$F_2$ | $SO_2CH_3$ | 129.5–130.5 |
| 6 | 4-$OCF_3$ | 4-CN | 2,5-$F_2$ | $COCH_3$ | 108–110.5 |
| 7 | H | 4-CN | 2,5-$F_2$ | H | 171–172.5 |
| 8 | 2-Cl | 4-CN | 2,5-$F_2$ | H | 165–167.5 |
| 9 | 4-$OCF_3$ | 4-CN | 2,5-$F_2$ | H | 165–167.5 |
| 10 | 3-CN | 4-CN | 2,5-$F_2$ | H | 196–197 |
| 11 | 3-F | 4-CN | 2,5-$F_2$ | H | 172–175.5 |
| 12 | 4-F | 4-CN | 2,5-$F_2$ | H | 165–167 |
| 13 | 2-F | 4-CN | 2,5-$F_2$ | H | 174–177 |
| 14 | 3-$CF_3$ | 4-CN | 2,5-$F_2$ | H | 195.5–199.5 |
| 15 | 3-Cl-4-$OCF_3$ | 4-CN | 2,5-$F_2$ | H | 136–136.5 |
| 16 | 4-$CF_3$ | 4-CN | 2,5-$F_2$ | H | 171–172 |
| 17 | 3-$CF_3$-4-Cl | 4-CN | 2,5-$F_2$ | H | 210–211 |
| 18 | 2-$CF_3$ | 4-CN | 2,5-$F_2$ | H | 184.5–186.5 |
| 19 | 2,4-$Cl_2$ | 4-CN | 2,5-$F_2$ | H | 182–186.5 |
| 20 | 4-Cl | 4-CN | 2,5-$F_2$ | H | 185–188 |
| 21 | 3,4-$Cl_2$ | 4-CN | 2,5-$F_2$ | H | 216–217.5 (decomposed) |
| 22 | 2,3-$Cl_2$ | 4-CN | 2,5-$F_2$ | H | 141–144.5 |
| 23 | 4-Br | 4-CN | 2,5-$F_2$ | H | 185–190 |
| 24 | H | 4-CN | 2,5-$F_2$ | $SO_2CH_3$ | 127.5–130 |
| 25 | H | 4-CN | 2,5-$F_2$ | 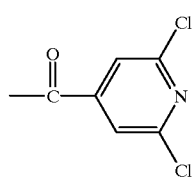 | 159–162 |
| 26 | 4-$OCF_3$ | 4-CN | 2,5-$F_2$ | $SO_2CH_3$ | 93–94.5 |
| 27 | 4-$CF_3$ | 4-CN | 2,5-$F_2$ | $COCH_3$ | 110–111 |

TABLE 1-continued

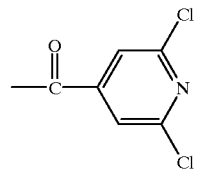

| Compound No. | R1n | R2 | R3m | R4 | melting point (° C.) or refractive index ($n^{20}_D$) |
|---|---|---|---|---|---|
| 28 | 4-OCF$_3$ | 4-CN | 2,5-F$_2$ | 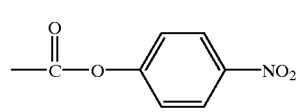 | 129.5–130.5 |
| 29 | 4-F | 4-CN | 2,5-F$_2$ | COCH$_3$ | 117.5–121.5 |
| 30 | 4-OCF$_3$ | 4-CN | 2-CF$_3$ | H | 137–138 |
| 31 | 4-F | 4-CN | 2-CF$_3$ | H | 149.5–151 |
| 32 | 3-CF$_3$ | 4-CN | 2-CF$_3$ | H | 176.5–178.5 |
| 33 | 3-Cl-4-CF$_3$ | 4-CN | 2-CF$_3$ | H | 170–171 |
| 34 | 4-CF$_3$ | 4-CN | 2-CF$_3$ | H | 152–152 |
| 35 | 3-CF$_3$-4-Cl | 4-CN | 2-CF$_3$ | H | 200–204.5 |
| 36 | 4-Cl | 4-CN | 2-CF$_3$ | H | 159.5–162.5 |
| 37 | 3,4-Cl$_2$ | 4-CN | 2-CF$_3$ | H | 175–176.5 |
| 38 | 2,3-Cl$_2$ | 4-CN | 2-CF$_3$ | H | 142–147 |
| 39 | 4-Br | 4-CN | 2-CF$_3$ | H | 168–171.5 |
| 40 | 2,6-Cl$_2$ | 4-CN | 2-CF$_3$ | H | 1.4720 |
| 41 | 3-Cl-4-CF$_3$ | 4-CN | 2-CF$_3$ | H | 172–174 (decomposed) |
| 42 | 3-Cl | 4-CN | 2-CF$_3$ | H | — |
| 43 | 3-F | 4-CN | 2-CF$_3$ | H | 149–151 |
| 44 | H | 4-CN | 2,5-F$_2$ | COOCH$_3$ | 113.5–115 |
| 45 | 3-CN | 4-CF$_3$ | 2,6-Cl$_2$ | H | 173–177 |
| 46 | 4-F | 4-CF$_3$ | 2,6-Cl$_2$ | H | 167–169 |
| 47 | 4-OCF$_3$ | 4-CF$_3$ | 2,6-Cl$_2$ | H | 128–132 |
| 48 | 4-OCF$_3$ | 4-CN | 2,5-F$_2$ | COOC$_2$H$_5$ | 87.5–88.5 |
| 49 | H | 4-CN | 2,5-F$_2$ | COCH$_2$OCH$_3$ | 85–85.5 |
| 50 | 4-OCF$_3$ | 4-CF$_3$ | 2-Cl-6-Br | H | 121–124 |
| 51 | H | 4-CN | 2,5-F$_2$ | CH$_3$ | 132–132.5 |
| 52 | 3-CF$_3$ | 4-CF$_3$ | 2,6-Cl$_2$ | H | 187–188 (decomposed) |
| 53 | 4-NO$_2$ | 4-CN | 2,5-F$_2$ | H | 178–180.5 |
| 54 | 3-Cl-4-OCF$_3$ | 4-CF$_3$ | 2,6-Cl$_2$ | H | 148–152 |
| 55 | 4-CF$_3$ | 4-CF$_3$ | 2,6-Cl$_2$ | H | 139.5–140 |
| 56 | 3-CF$_3$-4-Cl | 4-CF$_3$ | 2,6-Cl$_2$ | H | 132–136 |
| 57 | 4-OCF$_3$ | 2-CN | 3-F | H | 153–155.5 |
| 58 | 4-CF$_3$ | 2-CN | 3-F | H | 145.5–146.5 |
| 59 | 4-OCF$_3$ | 2-CN | 5-F | H | 138.5–140.5 |
| 60 | 4-OCF$_3$ | 4-CN | 2,5-F$_2$ | 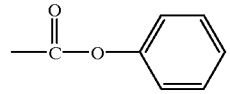 | 143.5–146.5 |
| 61 | 4-OCF$_3$ | 4-CN | 2,5-F$_2$ |  | 129.5–131.5 |
| 62 | 4-CF$_3$ | 2-CN | 5-F | H | 217–218 |
| 63 | 4-CF$_3$ | 2-CN | 5-Cl | H | 141–142 |
| 64 | 4-CF$_3$ | 4-CN | 2,6-Cl$_2$ | H | 191.5–193 (decomposed) |
| 65 | 4-CF$_3$ | 4-CF$_3$ | 2-Cl-6-Br | H | 192–193 |

TABLE 1-continued

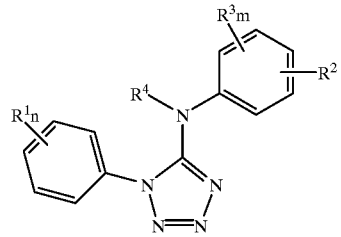

| Compound No. | $R^1n$ | $R^2$ | $R^3m$ | $R^4$ | melting point (° C.) or refractive index ($n^{20}_D$) |
|---|---|---|---|---|---|
| 66 | 4-CF$_3$ | 4-CN | 2,5-F$_2$ | COOCH$_3$ | 148.5–149.5 |
| 67 | 3-CF$_3$-4-Cl | 4-CF$_3$ | 2-Cl-6-Br | H | 162–163 |
| 68 | 4-OCF$_3$ | 4-CN | 2,5-F$_2$ | CH$_3$ | 111.5–112.5 |
| 69 | 4-OCF$_3$ | 4-CN | 2-F | H | 201.5–202.5 (decomposed) |
| 70 | 4-CF$_3$ | 4-CN | 2-F | H | 119–124 |
| 71 | 4-CF$_3$ | 2-CN | 3-F | H | 215–216 |
| 72 | 4-CF$_3$ | 4-CN | 2-Cl | H | 209–209.5 |
| 73 | 4-OCF$_3$ | 4-CN | 2-Cl | H | 183–186 |
| 74 | 4-Cl | 4-CN | 2,5-F$_2$ | CH$_3$ | 148–149.5 |
| 75 | 4-OCF$_3$ | 4-CN | 2,5-F$_2$ | CN | 155–157 |
| 76 | 4-Cl | 4-CF$_3$ | 2,6-Cl$_2$ | H | 156–160 |
| 77 | 3,4-Cl$_2$ | 4-CN | 2,5-F$_2$ | CH$_3$ | 150.5–152 |
| 78 | 2,3-Cl$_2$ | 4-CN | 2,5-F$_2$ | CH$_3$ | 148.5–149.5 |
| 79 | 3,4-Cl$_2$ | 4-CF$_3$ | 2,6-Cl$_2$ | H | 151–155 |
| 80 | 3,4-Cl$_2$ | 4-CN | 2-Cl | H | 230.5–232.5 (decomposed) |
| 81 | 3-Cl-4-CH$_3$ | 4-CN | 2-CF$_3$ | H | 148.5–152 |
| 82 | 4-CF$_3$ | 4-CN | 3-Cl | H | 207–210.5 (decomposed) |
| 83 | 3-Cl-4-OCF$_3$ | 4-CN | 3-Cl | H | 199–201.5 (decomposed) |
| 84 | 4-Br | 4-CN | 2,5-F$_2$ | CH$_3$ | 166–166.5 |
| 85 | 3-Cl-4-CF$_3$ | 4-CN | 2-Cl | H | 204.5–207.5 (decomposed) |
| 86 | 2-CH$_3$-4-Cl | 4-CN | 2-CF$_3$ | H | 153–155.5 |
| 87 | 2-Cl | 4-CN | 3-Cl | H | 219–223 (decomposed) |
| 88 | 4-CH$_3$ | 4-CN | 2-CF$_3$ | H | 109.5–112 |
| 89 | 3-CH$_3$-4-Br | 4-CN | 2-CF$_3$ | H | 101.5–104 |
| 90 | 2-Cl-5-CF$_3$ | 4-CN | 2-CF$_3$ | H | |
| 91 | 3-Cl-4-CF$_3$ | 4-CF$_3$ | 2-F-6-Cl | H | 117–121 |
| 92 | 4-CF$_3$ | 4-CF$_3$ | 2-F-6-Cl | H | 127.5–130 |
| 93 | 3-Cl-4-OCF$_3$ | 4-CF$_3$ | 2-F-6-Cl | H | 86.5–87.5 |
| 94 | 4-CF$_3$ | 2-CN | 3-Cl | H | 192–195 |
| 95 | 4-Cl | 4-CN | 2-F | H | 193–194 |
| 96 | 4-Br | 4-CN | 2-F | H | 182–186 |
| 97 | 4-Cl | 2-CN | 3-F | H | 173.5–174 (decomposed) |
| 98 | 4-Br | 2-CN | 3-F | H | — |
| 99 | 4-Br | 4-CF$_3$ | 2-Cl | H | 103.5–104.5 |
| 100 | 3-F | 4-CN | 2-CF$_3$ | H | 139.5–142.5 |
| 101 | 4-CF$_3$ | 4-CN | 2-Cl | CH$_3$ | 112–114 |
| 102 | 4-CF$_3$ | 4-CN | 2-OCF$_3$ | H | 120–123.5 |
| 103 | 4-Cl | 4-SO$_2$CF$_3$ | 2-Cl | H | 181–5.186.5 (decomposed) |
| 104 | 4-Br | 4-SO$_2$CF$_3$ | 2-Cl | H | 176–180 |
| 105 | 4-CF$_3$ | 4-SO$_2$CF$_3$ | 2-Cl | H | 159–162 |
| 106 | 4-F | 4-SO$_2$CF$_3$ | 2-Cl | H | 148–151 |
| 107 | H | 4-SO$_2$CF$_3$ | 2-Cl | H | — |
| 108 | 4-CF$_3$ | 4-SO$_2$CF$_3$ | 2-Cl | CH$_3$ | — |
| 109 | 4-CF$_3$ | 4-SO$_2$CH$_3$ | 2-Cl | H | — |
| 110 | 4-Cl | 4-SO$_2$CH$_3$ | 2-F | H | — |
| 111 | 4-Cl | 4-SO$_2$CH$_3$ | 2-Cl | H | — |
| 112 | 4-Br | 4-SO$_2$C$_2$H$_5$ | 2-Cl | H | — |
| 113 | 4-Cl | 4-SO$_2$CH$_3$ | 2,5-F$_2$ | H | — |
| 114 | 4-CF$_3$ | 4-NO$_2$ | 2-Cl | H | — |
| 115 | 4-CF$_3$ | 4-SO$_2$CH$_3$ | 2-Cl | CH$_3$ | — |
| 116 | 4-CF$_3$ | 4-CN | 2,5-F$_2$ | C$_2$H$_5$ | — |
| 117 | 4-CF$_3$ | 4-CN | 2-CF$_3$ | CH$_3$ | — |
| 118 | 3,4-F$_2$ | 4-CN | 2,5-F$_2$ | CH$_3$ | 123–125 |
| 119 | 4-CF$_3$ | 2-CF$_3$ | 4-Cl | H | 97–98 |
| 120 | 4-CF$_3$ | 2-CF$_3$ | 4-Cl | COOCH$_3$ | 115–119 |

TABLE 1-continued

| Compound No. | $R^1n$ | $R^2$ | $R^3m$ | $R^4$ | melting point (° C.) or refractive index ($n^{20}_D$) |
|---|---|---|---|---|---|
| 121 | 4-CF$_3$ | 2-CF$_3$ | 4-Br | H | 107–109 |
| 122 | 4-CF$_3$ | 2-CF$_3$ | 4-Br | COOCH$_3$ | 115–117 |
| 123 | 4-Cl | 4-CN | 2-OCF$_3$ | H | 134–135 |
| 124 | 4-SCF$_3$ | 4-CN | 2-CF$_3$ | H | 157–158 |
| 125 | 4-SCF$_3$ | 4-CN | 2-Cl | H | 153–156 |
| 126 | 4-Cl | 2-CN | 4-CF$_3$ | H | 149–153 |
| 127 | 4-SCF$_3$ | 4-CN | 2,5-F$_2$ | H | 157 |
| 128 | 4-Cl | 4-CF$_3$ | 2,5-Cl$_2$ | H | 150.5–156.5 |
| 129 | 4-Cl | 4-CF$_3$ | 2,5-F$_2$ | COOCH$_3$ | 1.5259 |
| 130 | 4-Cl | 4-CF$_3$ | 2,5-F$_2$ | H | — |
| 131 | 4-Cl | 4-CF$_3$ | 2,5-Cl$_2$ | H | — |
| 132 | 3-Cl-4-CH$_3$ | 4-CN | 3-F | H | 152–157 |
| 133 | H | 4-NO$_2$ | 2-Cl | H | — |
| 134 | 4-CF$_3$ | 4-NO$_2$ | 2-Cl | H | — |
| 135 | 4-CF$_3$ | 4-COOCH$_3$ | 2-Cl | H | — |
| 136 | 4-CF$_3$ | 2-COOCH$_3$ | 4-Cl | H | — |
| 137 | 4-Cl | 4-NO$_2$ | 2-Cl | H | — |
| 138 | 4-Br | 4-COOCH$_3$ | 2-Cl | H | — |
| 139 | 4-Cl | 4-CONH$_2$ | 2-Cl | H | — |
| 140 | 4-CF$_3$ | 4-CSNH$_2$ | 2,5-F$_2$ | H | — |
| 141 | 4-Cl | 4-CSNH$_2$ | 2,5-F$_2$ | H | — |
| 142 | 4-CF$_3$ | 4-COOC$_2$H$_5$ | 2,5-F$_2$ | H | — |
| 143 | 4-Cl | 4-COOC$_2$H$_5$ | 2,5-F$_2$ | H | — |
| 144 | 4-Cl | 4-NO$_2$ | 2-F | H | — |
| 145 | 4-CF$_3$ | 4-NO$_2$ | 2-Cl | CH$_3$ | — |
| 146 | 4-Cl | 4-COOCH$_3$ | 2-Cl | CH$_3$ | — |
| 147 | 4-CF$_3$ | 2-COOCH$_3$ | 4-Cl | CH$_3$ | — |
| 148 | 4-Cl | 4-COOCH$_3$ | 2,5-F$_2$ | CH$_3$ | — |
| 149 | 4-Cl | 4-COOCH$_3$ | 2,5-F$_2$ | H | — |
| 150 | 4-OCF$_3$ | 4-NOhd 2 | 2-Cl | H | — |
| 151 | H | 4-COOCH$_3$ | 2-Cl | H | — |
| 152 | 4-CF$_3$ | 4-COOCH$_3$ | 2-F | H | — |

USE EXAMPLES

Example 1

Fungicidal Test (Antimicrobial activity on culture medium)

Testing procedure

In this test, the pathogenic microorganisms shown below were used.

Plant pathogenic mold fungi:
  Pyricularia oryzae,
  Botrytis cinerea,
  Sclerotinia sclerotiorum,
Plant pathogenic bacteria:
  Xanthomonas campestris pv. oryzae
Animal pathogenic bacteria:
  Staphylococcus aureus, A potato-glucose agar culture medium was used for pre-cultivation and test of mold fungi, and a potato semi-synthetic culture medium was used for pre-cultivation and test of bacteria. Each testing compound dissolved in a small amount of methanol was suspended in distilled water and added to each medium at a concentration of 10 ppm. Fifteen ml of each medium to which the compound had been added was poured into a Petri dish (diameter: 9 cm) and solidified. Then, each testing microorganism was cultivated thereon. As for mold fungi, the pre-cultivated mycelial tuft was cut off with a cork borer (diameter: 4 mm) and the cut-off tuft was laid on a testing medium for cultivation. As for bacteria, a small amount of cells were inoculated into a medium with a platinum loop for streak cultivation. After 7 days of the cultivation for *Pyricularia oryzae* and after 2 days for the other pathogenic microorganisms, the diameter of mycelial tuft (mold fungi) or the degree of cell growth (bacteria) was measured to obtain a percent growth inhibition on the medium.

Results

Ninety nine % or higher antimicrobial activities were exhibited, respectively, by Compounds Nos. 9, 11, 12, 14, 16, 20, 23, 27 and 36 of the invention for *Pyricularia oryzae*; by Compounds Nos. 9, 11, 12, 14, 16, 20, 23, 27, 36 and 39 of the invention for *Botrytis cinerea*; by Compounds Nos. 9, 16, 20, 23 and 36 of the invention for *Sclerotinia sclerotiorum*; by Compounds Nos. 9, 16, 20, 23, 27, 36 and 39 of the invention for *Xanthomonas campestris* pv. oryzae; and by Compounds Nos. 9, 16, 20, 23, 36 and 39 of the invention for *Staphylococcus aureus*.

Fungicidal Test Example 2

(Petri dish test for gray mold)

Preparation of wettable powder

Active compound: 30 to 40 parts by weight

Carrier: a mixture of diatomaceous earth and kaolin (1:5), 55 to 65 parts by weight Emulsifier: polyoxyethylene alkyl phenyl ether, 5 parts by weight The above-stated amounts of active compound, carrier and emulsifier were pulverized and mixed to prepare wettable powder and the powder was diluted with water to each prescribed concentration of active compound.

Testing procedure

About three kidney beans (cultivar: serena) were sowed in a vinyl plastic pot (diameter: 7 cm) and raised in a greenhouse at 15 to 25° C. To small seedlings reaching a primary leaf stage, each testing compound which had been diluted at a prescribed concentration as mentioned above was applied in the amount of 25 ml per three pots. The mycelial tuft of *Botrytis cinerea* which had been cultivated in advance was cut off, together with the medium, with a cork borer to produce a tuft disc for inoculation. After 1 day from the application, the tuft disc was inoculated into the treated plants and kept in a humidity-temperature chamber of 20° C. After 4 days from the inoculation, occurrence rate in each pot was classified and evaluated according to the following criteria to calculate a control rate. The results are shown by the average evaluation of three pots.

| Occurrence rate | Ratio of spotted or blotched area (%) |
|---|---|
| 0 | 0 |
| 0.5 | less than 2 |
| 1 | 2 to less than 5 |
| 2 | 5 to less than 10 |
| 3 | 10 to less than 20 |
| 4 | 20 to less than 40 |
| 5 | 40 or more. |

Control rate (%)=(1-{occurrence rate in treated area÷occurrence rate in untreated area})×100

Results

Compounds Nos. 9, 16, 20, 23 and 28 of the invention exhibited 95% or higher control rate at the concentration of 250 ppm.

Insecticidal Test Example 1

(Test against *Spodoptera litura* larvae)

Preparation of test solutions

Solvent: 3 parts by weight of xylol

Emulsifier: 1 part by weight of polyoxyethylene alkyl phenyl ether

To produce a suitable preparation of active compound, 1 part by weight of active compound was mixed with the stated amount of solvent containing the stated amount of emulsifier, and the mixture was diluted with water to a prescribed concentration.

Testing procedure

Leaves of cabbage (*Bassica oleracea*) were dipped into the aqueous solution of the active compound at the prescribed concentration. After air-drying the solution, the treated leaves of cabbage were placed in a Petri dish (diameter: 9 cm), and ten of the third-instar larvae of common cutworms (*Spodoptera litura*) were released. The dish was then placed at an incubation chamber of 25° C. After 7 days, the number of dead larvae was examined to calculate mortality in %. Tests were successively conducted twice and the mortality in % is shown in their average.

Results

Compounds Nos. 1 to 5, 7 to 24, 26 to 39, 41 to 52, 60, 63, 65 to 67, 69 to 75, 77 to 81, 84 to 86, 88 to 106, 118 to 130 of the invention exhibited 100% of mortality at the concentration of 1000 ppm.

Insecticidal Test Example 2

(Test against *Aulacophora femoralis* larvae)

Testing procedure

Leaves of cucumber were dipped into the aqueous solution of the active compound at the prescribed concentration. After air-drying the solution, the treated leaves of cucumber were placed in a Petri dish (diameter: 9 cm), and ten of the second-instar larvae of cucurbit leaf beetles (*Aulacophora femoralis*) were released. The dish was then placed at an incubation chamber of 25° C. After 7 days, the number of dead larvae was examined to calculate mortality in %. Tests were successively conducted twice and the destruction in % is shown in their average.

Results

Compounds Nos. 1 to 5, 7 to 40, 41 to 44, 47 to 49, 51, 60 to 62, 66, 69 to 75, 77, 78, 81, 83 to 90, 93 to 106, 118 to 130 of the invention exhibited 100% of mortality at the concentration of 1000 ppm.

Herbicidal Test Example 1

(Herbicidal effect test against paddy field weeds)

Preparation of formulations of active ingredients carrier: acetone 5 parts by weight emulsifier: benzyloxy polyglycol ether 1 part by weight The formulations of active ingredients are obtained by mixing 1 part by weight of the active compounds and the above amounts of carrier and emulsifier. The prescribed amount of the formulation is diluted with water to prepare a testing formulation.

Testing procedure

In the greenhouse, each 3 seedlings of paddy rice (cultivar: Nihonbare) of 2.5 leaf stage (15 cm tall) were transplanted in two places in 1/2000 are large pot (25×25×9 cm) filled with paddy field soil. Then, seeds of small-flower, monochoria, broad-leaved weeds (common falsepimpernel, Indian toothcup, long stemmed water wort, *Ammannia multiflora* Roxb. *Dopatrium junceum* Hamilt, etc.) and bulrush were sowed, and water was poured on the soil to a depth of about 2–3 cm. Each prescribed amount of the formulation of active compound prepared similarly to those in the above preparation method, was applied to the surface of the water 7 days after the transplanting of the paddy rice.

The herbicidal effect and the degree of phytotoxicity against crop plants were examined on the day after 3 weeks from the treatment. During the test period the water depth of 3 cm was maintained. The herbicidal effect was rated as 100% in the case of complete death and as 0% in the case where no herbicidal effect was observed or in the case where no phytotoxicity was observed.

Results

In this test, for example, Compound Nos. 5, 6, 9, 11, 12, 16, 26, 27, 48 and 66 of the invention exhibited 90% or higher of the herbicidal rate against small-flower, monochoria, broad-leaved weeds and bulrush by application of 0.5 kg/ha of the amount of active compound.

Herbicidal Test Example 2

(Test of pre-emergence soil treatment against plowed land weeds)

Testing procedure

In the greenhouse, seeds of *Polygonum blumei Meissn* and *Amaranthus lividus* were sowed each in the surface layer of plowed land soil filled in a 120 cm² pot with soil-covering and each prescribed amount of the testing formulation prepared similarly to those in Herbicidal Test Example 1 was uniformly spread on the surface layer of soil in the testing pot.

The extent of herbicidal effect was examined after 4 weeks from spreading.

Results

In this test, for example, Compounds Nos. 5, 6, 16, 27, 28, 48 and 66 of the invention exhibited 100% of the herbicidal rate against *Polygonum blumei Meissn* and *Amaranthus lividus* by application of 0.5 kg/ha of the amount of active compound.

Herbicidal Test Example 3

(Test of post-emergence foliage treatment against plowed land weeds)

Testing procedure

In the greenhouse, seeds of *Polygonum blumei Meissn* and *Amaranthus lividus were sowed each in a* 120 cm² pot filled with plowed land soil and covered with soil. After 10 days from sowing and soil-covering (when the weeds were in 2-foliage stage on average), each prescribed amount of the formulation prepared similarly to those in Herbicidal Test Example 1 was uniformly spread on the foliage part of tested plant in the testing pot. After 3 weeks from spreading, the extent of herbicidal effect was examined.

Results

In this test, for example, Compounds Nos. 5, 28, 48 and 66 of the invention exhibited 90% or higher of the herbicidal rate against *Polygonum blumei Meissn* and *Amaranthus lividus* by application of 0.5 kg/ha of the amount of active compound.

Formulation Example 1

(granules)

Water (25 parts) is added to a mixture of Compound No. 3 of the invention (10 parts), bentonite (montmorillonite) (30 parts), talc (58 parts) and lignin sulphonate salt (2 parts) with well kneading and formed in 10–40 mesh granules using an extrusion-type granulator followed by drying at 40–50° C. to give granules.

Formulation Example 2

(granules)

A clay mineral (95 parts) having a particle size distribution within 0.2–2 mm range is introduced in a rotary mixer and Compound No. 1 of the invention (5 parts) is sprayed therein with a liquid diluents under rotation to uniformly wet followed by drying at 40–50° C. giving granules.

Formulation Example 3

(emulsion)

An emulsion is obtained by mixing Compound No. 3 of the invention (30 parts), xylene (5 parts), polyoxyethylene alkyl phenyl ether (8 parts) and calcium alkylbenzene sulphonate (7 parts) with stirring.

Formulation Example 4

(wettable powder)

A wettable powder is prepared by mixing Compound No. 5 of the invention (15 parts), a mixture (1:5) (80 parts) of White Carbon (fine powder of hydrated non-crystalline silicon oxide) and powdery clay, sodium alkylbenzene sulphonate (2 parts) and a condensate of sodium alkylnaphthalene sulphonate and formaldehyde (3 parts) in a powdery state.

Formulation Example 5

(wettable granules)

Wettable granules are prepared by thoroughly mixing Compound No. 2 of the invention (20 parts), sodium lignin sulphonate (30 parts), bentonite (15 parts) and calcined diatomaceous earth powder (35 parts) followed by addition of water and extrusion through a 0.3 mm screen and drying.

We claim:

1. 1-phenyl-5-anilinotetrazoles of the formula

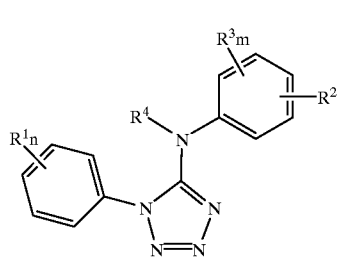

(I)

wherein
R¹ is hydrogen, halogen, cyano, nitro, $C_{1-4}$ alkyl, $C_{1-4}$ haloalkyl, $C_{1-4}$ haloalkoxy or $C_{1-4}$ haloalkylthio,
R² is cyano, nitro, $C_{1-4}$ haloalkyl, $C_{1-4}$ alkylsulfonyl, $C_{1-4}$ haloalkylsulfonyl, $C_{1-4}$ alkoxy-carbonyl, aminocarbonyl or aminothiocarbonyl,
R³ is halogen, $C_{1-4}$ haloalkyl or $C_{1-4}$ haloalkoxy,
R⁴ is hydrogen, cyano, $C_{1-4}$ alkyl, $C_{1-4}$ alkyl-carbonyl, $C_{1-4}$ alkoxy-carbonyl, $C_{1-4}$ alkylsulfonyl, $C_{1-4}$ alkoxy-$C_{1-4}$ alkyl-carbonyl, phenoxycarbonyl which may be substituted by nitro or pyridylcarbonyl which may be substituted by halogen,
n is 1, 2 or 3, and when n represents 2 or 3, two or three of R¹ may be same or different, and
m is 1 or 2, and when m represents 2, two of R³ may be same or different.

2. 1-phenyl-5-anilinotetrazoles of the formula (I) according to claim 1, in which
R¹ is hydrogen, halogen, cyano, nitro, $C_{1-3}$ alkyl, $C_{1-3}$ fluoroalkyl, $C_{1-3}$ fluoroalkoxy or $C_{1-3}$ fluoroalkylthio,
R² is cyano, nitro, $C_{1-3}$ haloalkyl, $C_{1-3}$ alkylsulfonyl, $C_{1-3}$ haloalkylsulfonyl, $C_{1-3}$ alkoxy-carbonyl, aminocarbonyl or aminothiocarbonyl, $R^3$ is halogen, $C_{1-3}$ fluoroalkyl or $C_{1-3}$ fluoroalkoxy, $R^4$ is hydrogen, cyano, $C_{1-3}$ alkyl, $C_{1-3}$ alkyl-carbonyl, $C_{1-3}$ alkoxy-carbonyl, $C_{1-3}$ alkylsulfonyl, $C_{1-2}$ alkoxy-$C_{1-2}$ alkyl-carbonyl, optionally nitro-substituted phenoxycarbonyl or optionally chloro-substituted pyridylcarbonyl, n is 1 or 2, and when n represents 2, two of $R^1$ may be same or different, and m is 1 or 2, and when m represents 2, two of $R^3$ may be same or different.

3. 1-phenyl-5-anilinotetrazoles of the formula (I) according to claim 1, in which $R^1$ is hydrogen, fluorine, chlorine, bromine, cyano, nitro, methyl, trifluoromethyl, trifluoromethoxy or trifluoromethylthio, $R^2$ is cyano, nitro, trifluoromethyl, methylsulfonyl, ethylsulfonyl, trifluoromethylsulfonyl, methoxycarbonyl, ethoxy-carbonyl, aminocarbonyl or aminothiocarbonyl, $R^3$ is fluorine, chlorine, bromine, trifluoromethyl or trifluoromethoxy, $R^4$ is hydrogen, cyano, methyl, methylcarbonyl, methoxycarbonyl, ethoxycarbonyl, methylsulfonyl, methoxymethylcarbonyl, phenoxycarbonyl, 4-nitrophenoxycarbonyl or 2,6-dichloro-4-pyridylcarbonyl, n is 1 or 2, and when n represents 2, two of $R^1$ may be same or different, and m is 1 or 2, and when m represents 2, two of $R^3$ may be same or different.

4. Process for the preparation of 1-phenyl-5-anilinotetrazoles of the formula (I),

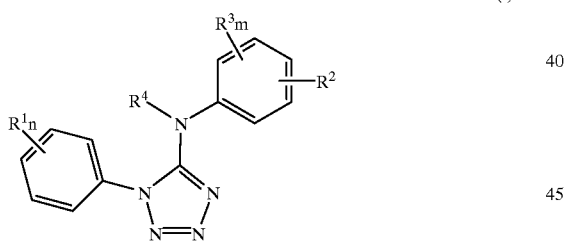

(I)

wherein $R^1$ is hydrogen, halogen, cyano, nitro, $C_{1-4}$ alkyl, $C_{1-4}$ haloalkyl, $C_{1-4}$-haloalkoxy or $C_{1-4}$ haloalkylthio, $R^2$ is cyano, nitro, $C_{1-4}$ haloalkyl, $C_{1-4}$ alkylsulfonyl, $C_{1-4}$ haloalkylsulfonyl, $C_{1-4}$ alkoxy-carbonyl, aminocarbonyl or aminothiocarbonyl, $R^3$ is halogen, $C_{1-4}$ haloalkyl or $C_{1-4}$ haloalkoxy, $R^4$ is hydrogen, cyano, $C_{1-4}$ alkyl, $C_{1-4}$ alkyl-carbonyl, $C_{1-4}$ alkoxy-carbonyl, $C_{1-4}$ alkylsulfonyl, $C_{1-4}$ alkoxy-$C_{1-4}$ alkyl-carbonyl, phenoxycarbonyl which may be substituted by nitro or pyridylcarbonyl which may be substituted by halogen, n is 1, 2 or 3, and when n represents 2 or 3, two or three of $R^1$ may be same or different, and m is 1 or 2, and when m represents 2, two of $R^3$ may be same or different, characterized in that a) in the case where $R^4$ is hydrogen:

compounds of the formula:

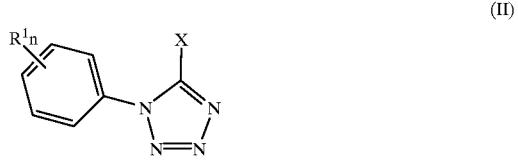

(II)

wherein $R^1$ and n are defined as above, and X is halogen or methylsulfonyl, are reacted with compounds of the formula:

(III)

wherein $R^2$, $R^3$ and m are defined as above, in the presence of inert solvents, and if, appropriate in the presence of an acid binder, or b) in the case where $R^4$ is $C_{1-4}$ alkyl or $C_{1-4}$ alkoxy-carbonyl:

compounds of the formula:

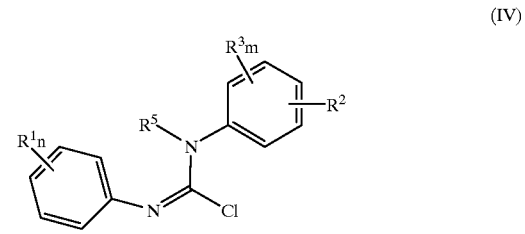

(IV)

wherein $R^1$, $R^2$, $R^3$, m and n are defined as above, and $R^5$ is $C_{1-4}$ alkyl or $C_{1-4}$ alkoxy-carbonyl, are reacted with sodium azide, in the presence of inert solvents, or c) in the case where $R^4$ is hydrogen:

compounds of the formula:

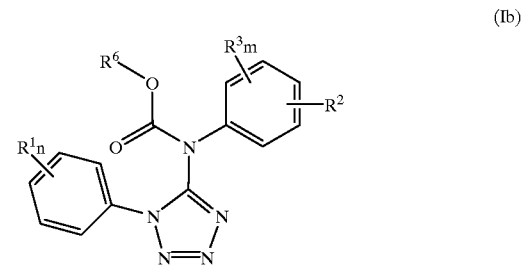

(Ib)

wherein $R^1$, $R^2$, $R^3$, n and m are defined as above, and $R^6$ is $C_{1-4}$ alkyl or optionally nitro-substituted phenyl, are hydrolyzed, in the presence of inert solvents, and, if appropriate, in the presence of a base, or d) in the case where $R^4$ is radicals as defined for the above $R^4$ with the exception of hydrogen and $C_{1-4}$ alkyl:

compounds of the formula:

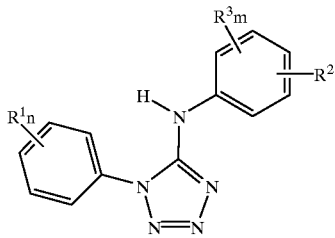

wherein $R^1$, $R^2$, $R^3$, n and m are defined as above, are reacted with compounds of the formula:

$$R^7-Y \qquad (V)$$

wherein $R^7$ is radicals as defined for the above $R^4$ with the exception of hydrogen and $C_{1-4}$ alkyl, and Y is halogen, preferably chlorine or bromine, in the presence of inert solvents, and, if appropriate, in the presence of an acid binder, or e) in the case where $R^4$ is $C_{1-4}$ alkyl-carbonyl or $C_{1-4}$ alkoxy-$C_{1-4}$ alkyl-carbonyl:

the above-mentioned compounds of the formula (Ia) are reacted with compounds of the formula:

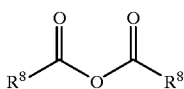

wherein $R^8$ is $C_{1-4}$ alkyl or $C_{1-4}$ alkoxy-$C_{1-4}$ alkyl, in the presence of inert solvents, and, if appropriate, in the presence of an acid catalyst.

5. An insecticidal composition comprising an insecticidally effective amount of a compound according to claim 1 and a diluent.

6. A microbiocidal composition comprising a microbiocidally effective amount of a compound according to claim 1 and a diluent.

7. An herbicidal composition comprising an herbicidally effective amount of a compound according to claim 1 and a diluent.

8. A method of combating unwanted pests which comprises administering to such pests or to a locus from which it is desired to exclude such pests a pesticidally effective amount of a compound according to claim 1.

9. A method of controlling unwanted microorganisms which comprises applying to such microorganisms or to a locus from which it is desired to exclude such microorganisms a microbiocidally effective amount of a compound according to claim 1.

10. A method of controlling unwanted vegetation which comprises administering to such vegetation or to a locus from which it is desired to exclude such vegetation an herbicidally effective amount of a compound according to claim 1.

* * * * *